(12) United States Patent
Bueschken et al.

(10) Patent No.: US 6,184,424 B1
(45) Date of Patent: Feb. 6, 2001

US006184424B1

(54) PROCESS FOR THE HYDROGENATION OF HYDROFORMYLATION MIXTURES

(75) Inventors: Wilfried Bueschken, Haltern; Dietmar Gubisch, Marl, both of (DE)

(73) Assignee: Oxeno Olefinchemie GmbH, Marl (DE)

( * ) Notice: Under 35 U.S.C. 154(b), the term of this patent shall be extended for 0 days.

(21) Appl. No.: 09/396,367

(22) Filed: Sep. 15, 1999

(30) Foreign Application Priority Data

Sep. 16, 1998 (DE) ................................................ 198 42 369

(51) Int. Cl.[7] .................................................... C07C 29/16
(52) U.S. Cl. ........................... 568/882; 568/883; 568/885; 568/907; 568/909; 568/909.5; 568/914
(58) Field of Search ..................................... 568/882, 883, 568/885, 907, 909, 909.5, 914

(56) References Cited

U.S. PATENT DOCUMENTS

| 5,399,793 | 3/1995 | Vargas et al. | 568/883 |
|---|---|---|---|
| 5,675,045 | 10/1997 | Bueschken et al. | 568/881 |
| 5,728,891 | 3/1998 | Bueschken et al. | 568/376 |
| 5,756,856 | 5/1998 | Bueschken et al. | 568/462 |
| 5,831,135 | 11/1998 | Bueschken et al. | 568/881 |
| 5,922,921 | * 7/1999 | Unruh et al. | 568/882 |

FOREIGN PATENT DOCUMENTS

| 931888 | 8/1955 | (DE) . |
|---|---|---|
| 1 935 900 | 2/1971 | (DE) . |
| 0 224 872 | 6/1987 | (EP) . |
| 35 42 595 A1 | 6/1987 | (DE) . |
| 0 850 905 A1 | 7/1998 | (EP) . |
| 2 322 119 | 3/1977 | (FR) . |

OTHER PUBLICATIONS

Kirk–Othmer, Encyclopedia of Chemical Technology, Fourth Edition, vol. 17, pp. 909–919, John Wiley & Sons.
New Syntheses with Carbon Monoxide, Edited by J. Falbe, Springer–Verlag, Berlin Heidelberg New York 1980, pp. 94–115 and pp. 164–165.

* cited by examiner

*Primary Examiner*—Peter O'Sullivan
(74) *Attorney, Agent, or Firm*—Oblon, Spivak, McClelland, Maier & Neustadt, P.C.

(57) ABSTRACT

A process for the hydrogenation of reaction mixtures from the hydroformylation of $C_5$ to $C_{24}$ olefins using hydrogen on fixed catalysts at elevated temperature, in which the aldehydes, alcohols, formates and low-boilers are evaporated from the reaction mixture and passed in the vapor state over a support-free Cu/Cr catalyst.

22 Claims, 1 Drawing Sheet

PROCESS FOR THE HYDROGENATION OF HYDROFORMYLATION MIXTURES

BACKGROUND OF THE INVENTION

1. Field of the Invention

The present invention relates to a process for the hydrogenation of hydroformylation mixtures from the preparation of higher oxo alcohols by hydroformylation of the corresponding olefins.

2. Description of the Background

Higher alcohols, in particular those having from 6 to 25 carbon atoms, can be prepared, as is known, by catalytic hydroformylation (or oxo reaction) of the olefins having one carbon atom less and subsequent catalytic hydrogenation of the aldehyde- and alcohol-containing reaction mixtures. They are predominantly used as starting materials for preparing plasticizers or detergents.

It is known that, in the catalytic hydroformylation of olefins, reaction mixtures are formed which, apart from the desired products, i.e. aldehydes and the corresponding alcohols, depending on the catalyst and the reaction conditions, can comprise by-products and secondary products, such as unreacted olefins, saturated hydrocarbons formed from the olefins by hydrogenation, water, esters of the desired alcohols (e.g. formates), acetals of the target products aldehyde and alcohol, enol ethers and other by-products or secondary products. These substances can be subdivided into low-boilers having a boiling point below the boiling point of the aldehyde and high-boilers having a boiling point above the boiling point of the alcohol. In the hydrogenation of the reaction mixtures, from some of the by-products, such as esters and acetals, the alcohols wanted as target product are formed, which improves the yield. In particular it is desired that the formates, which can occur in amounts up to 10% by weight, are hydrogenated under comparatively mild conditions and particularly at low pressure using commercially conventional catalysts to give the desired alcohol (and methanol as by-product).

The catalytic hydrogenation of reaction mixtures which were prepared by cobalt-catalyzed hydroformylation of olefins having from 2 to 24 carbon atoms is described, for example, in DE 35 42 595. The hydrogenation is carried out in two stages. In the first stage, the hydroformylation mixture is hydrogenated at 150–230° C. and a hydrogen pressure of 10–350 bar with 80–95% conversion on a supported $SiO_2$ catalyst which comprises 5–15% by weight of nickel and 2–20% by weight of molybdenum in the form of molybdenum oxide. In the second stage, the hydrogenation is completed at 150–230° C. and 10–350 bar hydrogen pressure on a catalyst whose active mass consists of 55–60% by weight of cobalt, 15–20% by weight of copper, 4–10% by weight of manganese and 2–5% by weight of molybdenum in the form of molybdenum oxide and, if appropriate, up to 10% by weight of activating additives. In the process; the formates and acetals present in the mixture are converted to the corresponding alcohols. However, the process has the disadvantage that the hydrogenation is carried out in two stages and at high pressures—in the example at 250 and 245 bar.

According to U.S. Pat. No. 5,399,793, for the hydrogenation of cobalt-depleted reaction mixtures, as arise in the hydroformylation of $C_5$–$C_{12}$ olefins, Ni/Mo catalysts on $Al_2O_3$ or $Al_2O_3.SiO_2$ as support materials are used. The complete process comprises the following individual steps:

(a) cobalt-catalyzed hydroformylation,
(b) cobalt depletion of the reaction mixture,
(c) hydrogenation of the crude reaction mixture at elevated temperature and at elevated pressure,
(d) production of alcohols having very low amounts of aldehydes by distillation, and
(e) finish-hydrogenation of the alcohols.

The hydrogenation of stages (c) and/or (e) can be carried out using a bimetallic, phosphorus-free Ni/Mo hydrogenation catalyst. This hydrogenation catalyst produces fewer high-boiling by-products than a corresponding phosphorus-containing catalyst. A disadvantage with this process is that to prepare an on-specification alcohol which is suitable for preparing plasticizers, two hydrogenation stages are necessary and that at least in the hydrogenation stage (b) a relatively high pressure of 1000 psig (about 70 bar) is necessary.

SUMMARY OF THE INVENTION

An object of the present invention is to provide a method to hydrogenate reaction mixtures of the hydroformylation of $C_5$ to $C_{24}$ olefins under comparatively mild conditions on conventional catalysts having a high service life in such a manner that the aldehydes and the formates present as by-products are converted into the desired alcohols.

This object, and others, is, surprisingly, accomplished with a process for the hydrogenation of reaction mixtures from the hydroformylation of $C_5$ to $C_{24}$ olefins, comprising:

evaporating the aldehydes, alcohols, formates and low-boilers from a reaction mixture obtained from the hydroformylation of $C_5$ to $C_{24}$ olefins to produce a vapor; and reacting the vapor with hydrogen in the presence of a support-free Cu/Cr catalyst.

BRIEF DESCRIPTION OF THE FIGURE

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
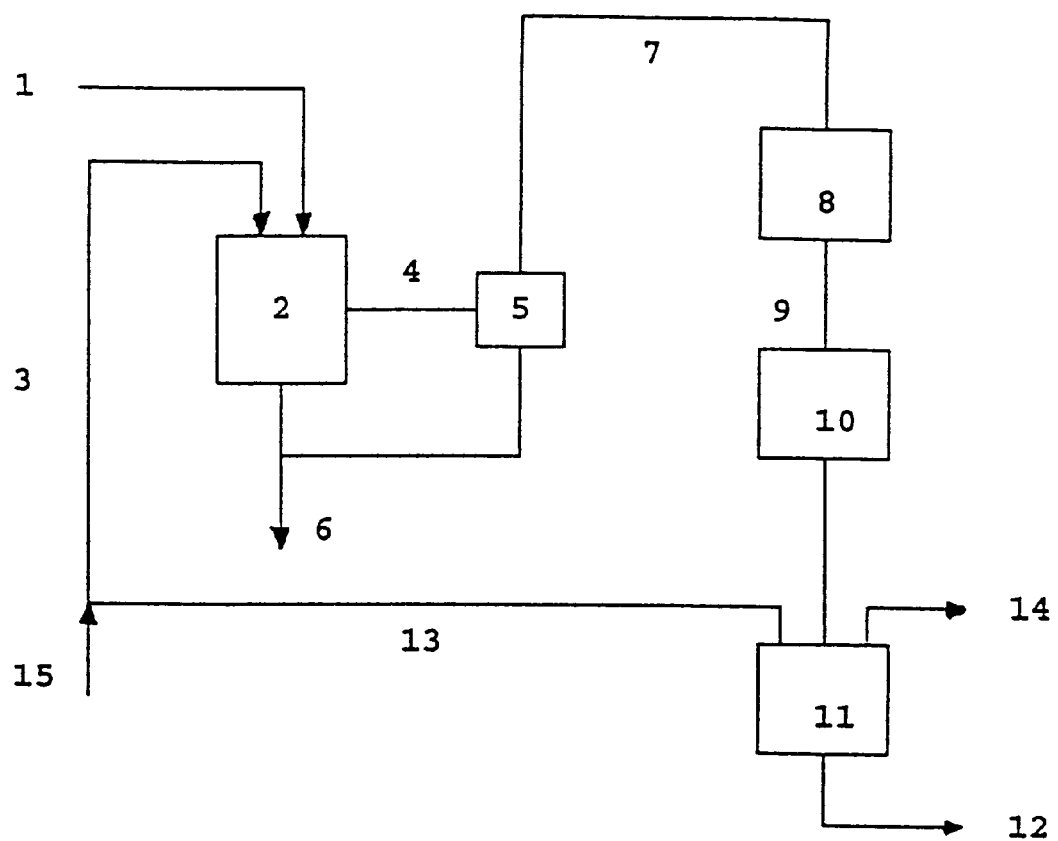
FIG. 1: A block diagram of the present process.

The process of the present invention provides a number of important advantages. The high-boilers entrained as droplets remaining in the evaporator and also advantageously separated off from the evaporated aldehydes, alcohols, formates and low-boilers are not co-hydrogenated, and do not therefore burden the hydrogenation stage. They can, for example, be worked up by cleavage or cracking to provide materials of value. The aldehydes are hydrogenated to the corresponding alcohols at conversion rates over 98% in a selectivity of above 99% in only one hydrogenation stage. The esters present, in particular the formates, are likewise hydrogenated to the desired alcohols. The hydrogenation can be performed in the low-pressure range of below 25 bar. A desired side effect is that the starting olefins present in the reaction mixture are predominantly not hydrogenated, which enables them to be recirculated to the hydroformylation reaction.

One advantage of the present invention is that the process may be conducted at low pressures. In addition, entrained droplets of high-boilers are separated off from the evaporated aldehydes, alcohols, formates and low-boilers upstream of the hydrogenation.

The FIGURE shows a block diagram of a plant in which the process according to the invention may be carried out continuously with recirculation as cycle gas of the hydrogenation hydrogen. The hydroformylation mixture is introduced as starting material 1 into the evaporator 2, through which heated hydrogen 3 passes concurrently. The hydrogen stream 4 loaded with aldehydes, alcohols, formates and low-boilers is conducted through the demister 5, and the high-boilers separated off there and those remaining in the evaporator 2 are taken off continuously or batchwise as high-boiler fraction 6. The hydrogen stream 7 which is freed from high-boilers and loaded with aldehydes, alcohols, formates and low-boilers is passed into the hydrogenation reactor 8, from which exits the hydrogenation mixture 9 which is cooled in the cooler 10. In the product receiver 11, the hydrogenation mixture separates into hydrogenation product 12 and cycle gas 13, from which a portion is taken off as exhaust gas 14, in order to keep the inert gas level to an acceptable height. The hydrogen consumed is replaced by fresh hydrogen 15.

The starting materials for the hydroformylation are monoolefins having from 5 to 24 carbon atoms and a terminal or middle-position C—C double bond or mixtures of such monoolefins, such as 1- or 2-pentene, 2-methyl-1-butane, 1-, 2- or 3-hexene, the isomeric $C_6$ olefin mixture (dipropene) produced in the dimerization of propene, 3-methyl-1-hexene, 1-octene, the isomeric $C_8$ olefin mixture (dibutene) produced in the dimerization of butenes, 1-nonene, 2-, 3- or 4-methyl-1-octane, the isomeric $C_9$ olefin mixture (tripropene) produced in the trimerization of propene, 1-, 2- or 3-decene, 2-ethyl- 1-octane, 1-dodecene, the isomeric $C_{12}$ olefin mixture (tetrapropene or tributene) produced in the tetramerization of propene or the trimerization of butenes, 1-tetradecene, 1- or 2-hexedecene, $C_{16}$ olefin mixtures (tetrabutene) produced in the tetramerization of butenes, and olefin mixtures prepared by cooligomerization of olefins having different carbon numbers (preferably 2 to 4), if appropriate after separating off by distillation into fractions of identical or similar carbon number. Preferably, mixtures are hydrogenated which are produced in the hydroformylation of $C_5$, $C_9$, $C_{12}$ or $C_{16}$ olefin mixtures.

The olefins are hydroformylated in a conventional manner and then give the starting materials for the hydrogenation process according to the invention. Rhodium catalysts, or preferably cobalt catalysts, are therefore employed, with or without complex-stabilizing additives, such as organic phosphines or phosphites. The temperatures and the pressures can vary, depending on catalyst and olefin, in broad ranges. A description of the hydroformylation of olefins is found, for example, in J. Falbe, New Syntheses with Carbon Monoxide, Springer-Verlag, Heidelberg-New York, 1980, pages 99ff., and in Kirk-Othmer, Encyclopedia of Chemical Technology, volume 17, 4th edition, John Wiley & Sons, pages 909–919 (1996), each incorporated herein by reference.

The hydroformylation reaction mixtures are preferably first separated from the catalyst. If a cobalt catalyst was used, this can be achieved by pressure relief, separating off the aqueous catalyst phase, oxidation of the cobalt carbonyl compounds remaining in the hydroformylation mixture with air or oxygen and scrubbing out the resulting cobalt compounds with water or aqueous acid. Cobalt-depletion processes are well known, see, for example, J. Falbe, loc. cit., 164, 165 (BASF process); Kirk-Othmer, loc. cit. and EP-0 850 905 A1, each incorporated herein by reference.

If a rhodium compound served as hydroformylation catalyst, it can be separated off from the hydroformylation mixture as distillation residue by means of thin-film evaporation.

The hydroformylation reaction mixtures, preferably separated from catalyst, generally comprise 3–40% by weight, usually 5–30% by weight, of low-boilers, in addition 30–90% by weight of aldehydes, 5–60% by weight of alcohols, up to 10% of formates of these alcohols and from 5 to 15% by weight of high-boilers. However, the process may also be carried out using hydroformylation mixtures having a composition other than as described above.

The aldehydes, alcohols, formates and low-boilers are then evaporated from the generally, undistilled hydroformylation reaction mixture, which if appropriate is separated from catalyst. The low-boilers particularly include unreacted olefins and the corresponding saturated hydrocarbons formed during the hydroformylation and water. The content of low-boilers in the reaction mixture varies within the limits mentioned above, depending on the starting olefin, the reaction conditions and the degree of conversion of the hydroformylation. The high-boilers which according to the invention are not to pass to the hydrogenation catalyst comprise, inter alia, aldolization and/or condensation products of the resulting aldehydes and also acetals and enol ethers and boil, as higher-molecular-weight substances, considerably higher than the alcohols, aldehydes, formates and low boilers.

The conditions under which aldehydes, alcohols, formates and low-boilers are separated from the high-boilers are considerably dependent on the carbon number of the starting olefins. The reaction mixture is preferably separated under the same conditions with respect to temperature and pressure under which the subsequent hydrogenation is carried out. The pressure is, therefore, generally below 25 bar. It is preferably from 1 to 25 bar, and in particular from 15 to 20 bar. In the case of reaction mixtures from the hydroformylation of olefins having from 6 to 12 carbon atoms (for example octenes which were obtained by dimerizing butanes), temperatures of, for example, from 150 to 250° C., advantageously from 160 to 220° C., can be employed. For other hydroformylation mixtures, the optimum temperature conditions for separating off the high-boilers can be determined without difficulty by simple trial runs.

To separate the hydroformylation mixtures, use is made of conventional apparatuses, e.g. thin-film evaporators or falling-film evaporators. In an one embodiment, the mixture is added to a hydrogen stream of appropriate temperature. Independently of the evaporation method selected, it is preferable to free the vapor stream from high-boiler droplets, since in this manner the service life of the catalyst is increased. Conventional demisters may be used, in which the velocity of the vapor stream is decreased, the vapor stream is exposed to the action of centrifugal forces or the droplets are separated off by impact, e.g. on baffles or screens.

If the hydroformylation mixture was evaporated by introduction into a heated hydrogen stream, the hydrogen/vapor mixture is conducted over the catalyst. Otherwise, hydrogen is added to the vapor mixture. The hydrogen is preferably used in a considerable stoichiometric excess Advantageously, a hydrogen:starting material mass ratio of from 3.5:1 to 0.7:1, in particular from 3:1 to 1:1, is employed. The unconsumed hydrogen may be recirculated.

The catalyst is a support-free Cu/Cr catalyst. It is preferably used as a fixed-bed catalyst and generally comprises from 25 to 40% by weight of copper and from 18 to 30% by weight of chromium. The catalyst can comprise up to 20% by weight of basic substances, such as alkali metal oxides or alkaline earth metal oxides or alkali metal hydroxides or alkaline earth metal hydroxides, and other, inert or property-modifying substances in the same amounts, for example graphite. As used herein, the term "support-free" refers to the absence of support material which has been sprayed or impregnated with a solution of the active components or onto which the active components have been adhesively applied in another manner. The initially oxidic catalyst is expediently reduced by passing over hydrogen at elevated temperature, e.g. the hydrogenation temperature, and then develops its optimum activity. The specified percentages by weight relate to the oxidic, unreduced form of the catalyst. Suitable catalysts are, for example, the catalyst E406TU from Mallinckrodt, Erie, Pa. U.S.A., and the catalyst G99B from Süd-Chemie A G, 80333 Munich. The catalysts are expediently used in a form which offers a low resistance to flow, e.g. in the form of granules, pellets or shaped bodies such as tablets, cylinders, rod extrudates or rings. Temperatures at the catalyst and the pressure advantageously correspond, as mentioned, to the conditions under which the aldehydes, alcohols, formates and low-boilers are evaporated from the hydroformylation mixture.

The optimum temperature in the catalyst bed is preferably determined for a given hydroformylation mixture by preliminary experiments. In the hydroformylation mixtures which were obtained by hydroformylation of olefins having from 6 to 12 carbon atoms, it is, as mentioned, from 150 to 250° C., advantageously from 160 to 220° C. It is expedient that the temperature of the cycle gas comprising the evaporated portion of the hydroformylation mixture at the inlet of the hydrogenation reactor is at least as high as at the outlet of the demister. Advantageously, it is therefore provided that the cycle gas in this process section can be heated, expediently can be indirectly heated, and can be thermostated.

The hydrogenation generally proceeds exothermically. The reaction can be conducted adiabatically with temperature increase. Alternatively, it is also possible to arrange the hydrogenation essentially isothermically, i.e., to permit a temperature rise of only up to 10° C. from the reactor inlet to the exit of the hydrogenation mixture. In the latter case, the temperature is expediently controlled by feeding cold hydrogen.

The process according to the invention permits high throughputs. The liquid hourly space velocity (LHSV) of the catalyst is given as the hourly volumetric flow of the still liquid starting material divided by the catalyst volume. It depends, inter alia, on the temperature selected and is generally between 0.07 h$^{-1}$ and 0.40 h$^{-1}$, in particular between 0.12 h$^{-1}$ and 0.25 h$^{-1}$. The residence time of the gas phase in the catalyst zone essentially depends on the GHSV (gas hourly space velocity), the temperature selected and the pressure and can be, for example, between 3 and 30 seconds.

The hydrogenation mixture can, after separating off excess hydrogen, be fractionated into its constituents by fractional condensation or by complete condensation and distillation. The non-hydrogenated olefins can be recovered from the low-boiler fraction, advantageously by distillation, and recirculated into the hydroformylation. Alternatively, the olefins, together with the saturated hydrocarbons formed from them in the hydroformylation or the hydrogenation can be used as raw material for crackers or for heating purposes. This is the case especially if the hydroformylation was operated with high conversion of the starting olefins. The alcohols are produced in a purity of >99%, determined by gas-chromatographic analysis. The residue can be combined with the high-boilers, which remained in the evaporation of the aldehydes, alcohols, formates and low-boilers, and can be worked up together with them to materials of value. For example, by cracking, olefins can be produced which in turn can be hydroformylated.

Having generally described this invention, a further understanding can be obtained by reference to certain specific examples which are provided herein for purposes of illustration only and are not intended to be limiting unless otherwise specified.

EXAMPLES

Example 1

As starting material 1, hydroformylated di-n-butene was fed by a metering pump into the evaporator 2 of a gas-phase hydrogenation apparatus according to the FIGURE, into a hydrogen stream 3 heated to 200° C. The hydrogen stream 4 which leaves the evaporator and is loaded with aldehydes, alcohols, formates and low-boilers and comprises high-boiler droplets was passed through the demister 5 and, after separating off high-boilers, was passed as material stream 7 to the top of the hydrogenation reactor 8. The high-boilers 6 remaining in the evaporator and separated off in the demister 5 were taken off every 12 h.

The reactor was a steel tube of 38 mm open width, in which 800 ml (=1200 g) of the catalyst E406TU from Mallinckrodt had been arranged, fixed, in the form of pellets. The catalyst in its oxidic unreduced form, comprised 42% by weight of CuO, equivalent to 33.55% by weight of Cu 40% by weight of $Cr_2O_3$ equivalent to 27.37% by weight of Cr 8% by weight of BaO and 10% by weight of graphite.

The catalyst was reduced by 2500 l(S.T.P.)/h of nitrogen firstly being passed, at 150° C. and 1 bar, over 800 ml of catalyst. A maximum of 5% of the nitrogen was replaced by hydrogen and the gas stream was controlled in such a manner that the temperature rise remained below 10° C. After 2 h in each case, the volumetric concentration of the hydrogen was increased by 5%. After reduction had finally been carried out using pure hydrogen, the temperature was elevated to 160° C. After a further 2 h in each case, the temperature was increased each time by 10° C. After a temperature of 190° C. had been reached, the hydrogen pressure was elevated stepwise to 15 bar under strict temperature control and the catalyst was kept under these conditions for 12 h.

The hydrogenation mixture was cooled in the cooler 10. The condensed hydrogenation product 12 was taken off from the receiver 11, the cycle gas 13 recirculated to the evaporator and some of the cycle gas was taken off as exhaust gas 14. Consumed hydrogen was replaced by fresh hydrogen 15.

The process was carried out under the following conditions:

| | |
|---|---|
| Starting material fed | 160 g/h |
| Fresh hydrogen fed | 62 l(S.T.P.)/h |
| Cycle hydrogen gas | 2500 l(S.T.P.)/h |
| Exhaust gas | 50 l(S.T.P.)/h |
| High-boilers | 3 g/h |
| Temperature downstream of the evaporator | 180° C. |
| Temperature at the hydrogenation reactor inlet | 185° C. |
| Temperature in the hydrogenation reactor | 185° C. |

-continued

| | |
|---|---|
| Pressure in the system | 16 bar |
| Hydrogenation product approximately | 158 g/h |

GC analyses of the starting material and of the hydrogenation product gave the following values:

| Substance | Starting material (% by weight) | Product (% by weight) |
|---|---|---|
| Isononanals | 39.4 | 0.2 |
| Isononanols | 41.8 | 87.9 |
| Isononyl formates | 4.2 | <0.1 |
| High-boilers | 5.9 | 2.2 |

After operation for one week, a steady state was reached and the product composition remained the same for a period of more than 6 months.

Example 2

When the same experiment was carried out without a demister under otherwise identical conditions, as soon as after 6 weeks a markedly impaired hydrogenation performance was observed, recognizable by a higher content of isononyl formates.

Obviously, numerous modifications and variations of the present invention are possible in light of the above teachings. It is therefore to be understood that within the scope of the appended claims, the invention may be practiced otherwise than as specifically described herein.

German Patent Application Serial No. 19842369.1 filed on Sep. 16, 1998, is incorporated herein by reference.

What is claimed is:

1. A process for the hydrogenation of reaction mixtures from the hydroformylation of $C_5$ to $C_{24}$ olefins, comprising:
   evaporating the aldehydes, alcohols, formates and low-boilers from a reaction mixture obtained from the hydroformylation of $C_5$ to $C_{24}$ olefins to produce a vapor; and
   reacting the vapor with hydrogen in the presence of a support-free Cu/Cr catalyst.

2. The process of claim 1, wherein the process is carried out continuously.

3. The process of claim 1, wherein, using a demister, entrained droplets of high-boilers are separated off from the evaporated aldehydes, alcohols, formates and low-boilers upstream of the hydrogenation.

4. The process of claim 3, wherein the high-boilers produced in the demister and in the evaporator are worked up to materials of value.

5. The process of claim 3, wherein the cycle gas, after leaving the demister and upstream of entry into the hydrogenation reactor, is heated and thermostated.

6. The process of claim 3, wherein the temperature of the cycle gas at the inlet of the hydrogenation reactor is at least as high as at the outlet of the demister.

7. The process of claim 1, wherein the catalyst comprises from 25 to 40% by weight of Cu and from 18 to 30% by weight of Cr, based on the oxidic form of the catalyst.

8. The process of claim 7, wherein the catalyst comprises up to 20% by weight of a basic substance.

9. The process of claim 8, wherein the catalyst comprises up to 20% by weight of an inert or property-modifying substance.

10. The process of claim 1, wherein the hydrogenation is carried out on a fixed-bed catalyst.

11. The process of claim 1, wherein the hydrogenation is conducted at from 150 to 250° C.

12. The process of claim 1, wherein the hydrogenation is conducted from 160 to 220° C.

13. The process of claim 1, wherein the hydrogenation is conducted adiabatically.

14. The process of claim 1, wherein the hydrogenation is essentially conducted isothermically, by controlling the temperature by feeding cold gas.

15. The process of claim 1, wherein the hydrogenation is conducted at a pressure of from 1 to 25 bar.

16. The process of claim 1, wherein the hydrogenation is conducted at a pressure of from 15 to 20 bar.

17. The process of claim 1, wherein the liquid hourly space velocity of the catalyst is between 0.07 $h^{-1}$ and 0.40 $h^{-1}$.

18. The process of claim 1, wherein the liquid hourly space velocity of the catalyst is between 0.12 $h^{-1}$ and 0.25 $h^{-1}$.

19. The process of claim 1, wherein the hydrogenation is conducted at a hydrogen:starting material mass ratio of from 35:1 to 07:1.

20. The process of claim 1, wherein the hydrogenation is conducted at a hydrogen:starting material mass ratio of from 3:1 to 1:1.

21. The process of claim 1, wherein the hydroformylation reaction mixture is obtained by cobalt-catalyst hydroformylation.

22. The process of claim 21, wherein the hydroformylation reaction mixture is undistilled.

* * * * *